United States Patent [19]
Hunter

[11] Patent Number: 6,021,254
[45] Date of Patent: Feb. 1, 2000

[54] TIMED ELECTRIC VEHICULAR AIR FRESHENER

[76] Inventor: James R. Hunter, 619 N. Juanita Ave. #D, Redondo Beach, Calif. 90277

[21] Appl. No.: 09/018,993

[22] Filed: Feb. 5, 1998

[51] Int. Cl.[7] .................................................. A61M 16/00
[52] U.S. Cl. ........................ 392/390; 392/386; 392/389; 261/DIG. 65
[58] Field of Search .................................... 392/386, 387, 392/388, 389, 390; 261/DIG. 65

[56] References Cited

U.S. PATENT DOCUMENTS

| | | | |
|---|---|---|---|
| 3,551,092 | 12/1970 | Masson | 21/119 |
| 4,574,181 | 3/1986 | Spector | 219/274 |
| 4,686,353 | 8/1987 | Spector | 219/275 |
| 4,692,590 | 9/1987 | Spector | 219/275 |
| 4,808,347 | 2/1989 | Dawn | 261/30 |
| 4,968,456 | 11/1990 | Muderlak et al. | 261/30 |
| 5,373,581 | 12/1994 | Smith | 392/390 |
| 5,394,506 | 2/1995 | Stein et al. | 392/395 |
| 5,424,049 | 6/1995 | Giolitti et al. | 422/305 |
| 5,432,882 | 7/1995 | Glynn | 392/392 |
| 5,788,931 | 8/1998 | Munoz Quintana | 422/125 |

*Primary Examiner*—Mark Paschall
*Assistant Examiner*—Shawntina Fuqua

[57] ABSTRACT

A heat released vehicular air freshener is provided including a power unit for being releasably received in electrical communication with a vehicular cigarette lighter. Also included is a fragrance mechanism mounted on the power unit for dispensing an aroma when actuated. An actuation assembly includes a timer mechanism for actuating the fragrance mechanism for a predetermined amount of time when actuated.

5 Claims, 2 Drawing Sheets

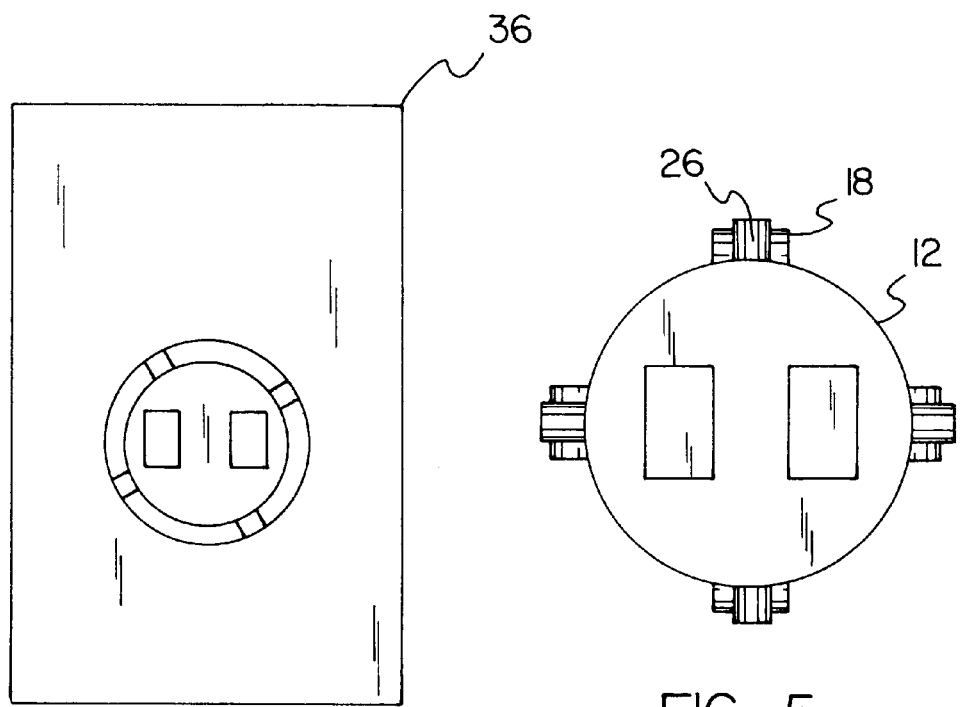
FIG. 4
FIG. 5
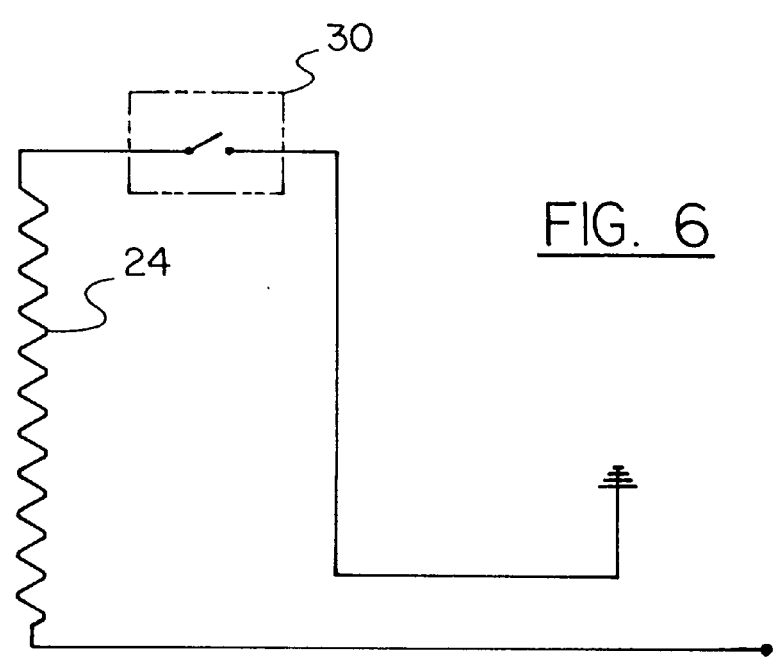
FIG. 6

TIMED ELECTRIC VEHICULAR AIR FRESHENER

BACKGROUND OF THE INVENTION

1. Field of the Invention

The present invention relates to air fresheners and more particularly pertains to a new timed electric vehicular air freshener for automatically deactuating an air freshener upon the cessation of a predetermined amount of time.

2. Description of the Prior Art

The use of air fresheners is known in the prior art. More specifically, air fresheners heretofore devised and utilized are known to consist basically of familiar, expected and obvious structural configurations, notwithstanding the myriad of designs encompassed by the crowded prior art which have been developed for the fulfillment of countless objectives and requirements.

Known prior art air fresheners include U.S. Pat. No. 5,394,506; U.S. Pat. No. 5,373,581; U.S. Pat. No. 4,686,353; U.S. Pat. No. 4,686,353; U.S. Pat. No. 5,171,485; U.S. Pat. Des. 306,644; and U.S. Pat. No. 4,808,347.

In these respects, the timed electric vehicular air freshener according to the present invention substantially departs from the conventional concepts and designs of the prior art, and in so doing provides an apparatus primarily developed for the purpose of automatically deactuating an air freshener upon the cessation of a predetermined amount of time.

SUMMARY OF THE INVENTION

In view of the foregoing disadvantages inherent in the known types of air fresheners now present in the prior art, the present invention provides a new timed electric vehicular air freshener construction wherein the same can be utilized for automatically deactuating an air freshener upon the cessation of a predetermined amount of time.

The general purpose of the present invention, which will be described subsequently in greater detail, is to provide a new timed electric vehicular air freshener apparatus and method which has many of the advantages of the air fresheners mentioned heretofore and many novel features that result in a new timed electric vehicular air freshener which is not anticipated, rendered obvious, suggested, or even implied by any of the prior art air fresheners, either alone or in any combination thereof.

To attain this, the present invention generally comprises a power unit with an inboard extent with a cylindrical configuration. The inboard extent of the power unit includes an inboard face with a spring biased post contact mounted thereon. An outboard face of the inboard extent is equipped with a first pair of contacts mounted thereon. Four resilient arcuate contacts are mounted on a periphery of the inboard extent for being releasably received in electrical communication with a vehicular cigarette lighter. The power unit further includes an outboard extent having a cylindrical sleeve slidably mounted over the outboard face of the inboard extent. Note FIG. 1. The sleeve has a second pair of contacts mounted on an inner surface thereof for communicating with the first pair of contacts of the inboard extent only upon the depression thereof, as shown in FIG. 1. A heater coil is mounted within the sleeve adjacent to an outboard face of the outboard extent. Such heater is connected to the second pair of contacts for generating heat upon the receipt of power. For reasons that will soon become apparent, a periphery of the sleeve has four equally spaced posts extending radially therefrom. Next provided is an actuation assembly including a timer mechanism situated within the inboard extent of the power unit. The timer is electrically connected between the spring biased post contact, resilient arcuate contacts, and the first pair of contacts for supplying power to the second pair of contacts and heater coil upon the depression of the sleeve. A timer is started for a predetermined amount of time upon the depression of the sleeve. The actuation assembly further includes a solenoid, or other means for separating the first and second pair of contacts upon the cessation of the predetermined amount of time. Finally, a fragrance mechanism includes a housing having a rectangular configuration. The housing has an interior space with a fragrance material positioned therein. As shown in FIG. 2, a front face of the housing is equipped with a plurality of parallel horizontally oriented vents formed therein. The housing further has a rear face with a tubular sleeve mounted thereon having an open rear face. Further, four equally spaced L-shaped cut outs are formed in a periphery of the tubular sleeve. These cut outs function for releasably coupling with the posts of the power unit. In operation, the fragrance mechanism serves for generating an aroma when the fragrance material is heated.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new timed electric vehicular air freshener apparatus and method which has many of the advantages of the air fresheners mentioned heretofore and many novel features that result in a new timed electric vehicular air freshener which is not anticipated, rendered obvious, suggested, or even implied by any of the prior art air fresheners, either alone or in any combination thereof.

It is another object of the present invention to provide a new timed electric vehicular air freshener which may be easily and efficiently manufactured and marketed.

It is a further object of the present invention to provide a new timed electric vehicular air freshener which is of a durable and reliable construction.

An even further object of the present invention is to provide a new timed electric vehicular air freshener which is susceptible of a low cost of manufacture with regard to both materials and labor, and which accordingly is then susceptible of low prices of sale to the consuming public, thereby making such timed electric vehicular air freshener economically available to the buying public.

Still yet another object of the present invention is to provide a new timed electric vehicular air freshener which provides in the apparatuses and methods of the prior art some of the advantages thereof, while simultaneously overcoming some of the disadvantages normally associated therewith.

Still another object of the present invention is to provide a new timed electric vehicular air freshener for automatically deactuating an air freshener upon the cessation of a predetermined amount of time.

Even still another object of the present invention is to provide a new timed electric vehicular air freshener that includes a power unit for being releasably received in electrical communication with a vehicular cigarette lighter. Also included is a fragrance mechanism mounted on the power unit for dispensing an aroma when actuated. An actuation assembly includes a timer mechanism for actuating the fragrance mechanism for a predetermined amount of time when actuated.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is a cross-sectional view of the present invention shown in FIG. 1 showing the second pair of contacts.

FIG. 5 is a cross-sectional view of the present invention shown in FIG. 1 showing the first pair of contacts.

FIG. 6 is a schematic diagram of the present invention.

DESCRIPTION OF THE PREFERRED EMBODIMENT

Figure 1:
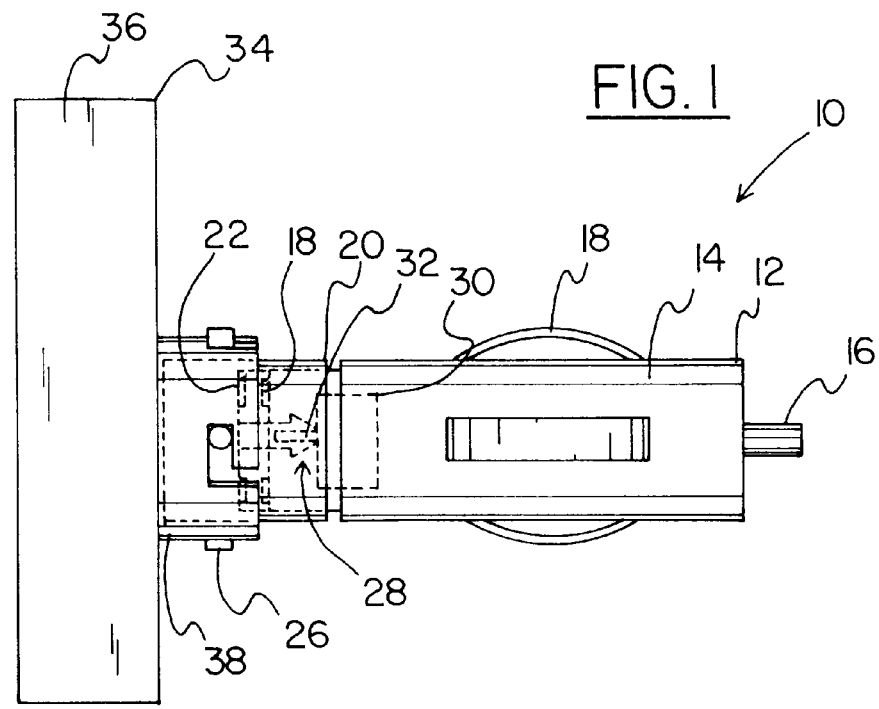
FIG. 1 is a side view of a new timed electric vehicular air freshener according to the present invention.

With reference now to the drawings, and in particular to FIGS. 1 through 6 thereof, a new timed electric vehicular air freshener embodying the principles and concepts of the present invention and generally designated by the reference numeral 10 will be described.

The present invention, designated as numeral 10, includes a power unit 12 with an inboard extent 14 with a cylindrical configuration. The inboard extent of the power unit includes an inboard 54 face with a spring biased post contact 16 mounted thereon. An outboard 56 face of the inboard extent is equipped with a first pair of contacts 18 mounted thereon. Four resilient arcuate contacts 52 are mounted on a periphery of the inboard extent for being releasably received in electrical communication with a vehicular cigarette lighter.

The power unit further includes an outboard extent having a cylindrical sleeve 20 slidably mounted over the outboard face of the inboard extent. Note FIG. 1. As shown in FIG. 1, the sleeve has a length less than ¼ that of the inboard extent of the power unit. Further, the sleeve has a second pair of contacts 22 mounted on an inner surface thereof for communicating with the first pair of contacts of the inboard extent only upon the depression thereof, as shown in FIG. 1. A heater coil 24 is mounted within the sleeve adjacent to an outboard face of the outboard extent. Such heater is connected to the second pair of contacts for generating heat upon the receipt of power. For reasons that will soon become apparent, a periphery of the sleeve has four equally spaced posts 26 extending radially therefrom.

Next provided is an actuation assembly 28 including a timer mechanism 30 situated within the inboard extent of the power unit. The timer mechanism is electrically connected between the spring biased post contact, resilient arcuate contacts, and the first pair of contacts for supplying power to the second pair of contacts and heater coil upon the depression of the sleeve. A timer is started for a predetermined amount of time upon the depression of the sleeve. This is preferably accomplished by way of a push button or the like mounted on the outboard face of the inboard extent of the power unit.

The actuation assembly further includes a solenoid 32, or other means for separating the first and second pair of contacts upon the cessation of the predetermined amount of time. It should be noted that the contacts may be maintained in communication by way of friction between the extents of the power unit. In various alternate embodiments, the solenoid may be excluded and a spring may used to urge the contacts apart and an electromagnetic coupling mechanism may be used to maintain communication therebetween until the timer is terminated.

Figures 2, 3:
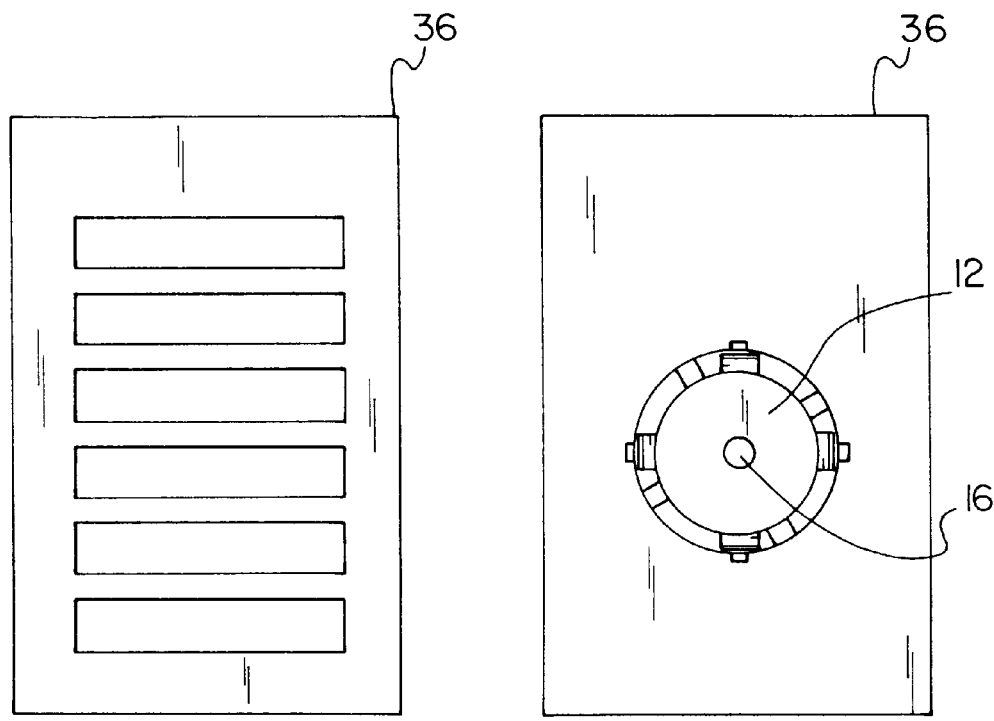
FIG. 2 is a front view of the fragrance mechanism of the present invention.
FIG. 3 is a rear view of the fragrance mechanism of the present invention.

Finally, a fragrance mechanism 34 includes a housing 36 having a rectangular configuration. The housing has an interior space with a fragrance material positioned therein. As shown in FIG. 2, a front face of the housing is equipped with a plurality of parallel horizontally oriented vents formed therein. The housing further has a rear face with a tubular sleeve 38 mounted thereon having an open rear face. Further, four equally spaced L-shaped cut outs are formed in a periphery of the tubular sleeve. These cut outs function for releasably coupling with the posts of the power unit. In operation, the fragrance mechanism serves for generating an aroma when the fragrance material is heated.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A heat released vehicular air freshener comprising, in combination:

a power unit including an inboard extent and an outboard extent, said inboard extent having a cylindrical configuration, said cylindrical configuration having an inboard face with a spring biased post contact mounted on the inboard face, said cylindrical configuration having an outboard face with a first pair of contacts mounted on said outboard face, said cylindrical configuration having a periphery having four resilient arcuate contacts for being releasably received in electrical communication with a vehicular cigarette lighter, said resilient arcuate contacts being positioned in spaced relationship to each other around said periphery of said cylindrical configuration, the power unit further including an outboard extent including a cylindrical sleeve slidably mounted over the outboard face of the inboard extent, the sleeve having a second pair of contacts mounted on an inner surface thereof for communicating with the first pair of contacts of the inboard extent only upon the depression thereof, a heater mounted within the sleeve adjacent to an outboard face of the outboard extent and connected to the second pair of contacts for generating heat upon the receipt of power, wherein a periphery of the sleeve has four equally spaced posts extending radially therefrom;

an actuation assembly including a timer mechanism situated within the inboard extent of the power unit and electrically connected between the spring biased post contact, resilient arcuate contacts, and the first pair of contacts for supplying power to the second pair of contacts and heater coil and starting a timer for a predetermined amount of time upon the depression of the sleeve, the actuation assembly further including a solenoid for separating the first and second pair of contacts upon the cessation of the predetermined amount of time; and a fragrance mechanism including a housing having a rectangular configuration and including an interior space with a fragrance material positioned therein, a front face with a plurality of parallel horizontally oriented vents formed therein, and a rear face with a tubular sleeve mounted thereon having an open rear face and four equally spaced L-shaped cut outs formed in a periphery thereof for releasably coupling with the posts of the power unit such that depression of said fragrance mechanism urges said first pair of contacts into contact with said second pair of contacts and further generating an aroma when the fragrance material is heated.

2. A heat released vehicular air freshener comprising, in combination:

a power unit for being releasably received in electrical communication with a vehicular cigarette lighter, said power unit including an inboard extent and an outboard extent, said inboard extent having a cylindrical configuration, said cylindrical configuration having an inboard face with a spring biased post contact mounted on the inboard face, said cylindrical configuration having an outboard face with a first pair of contacts mounted on said outboard face, said cylindrical configuration having a periphery having four resilient arcuate contacts for being releasably received in electrical communication with a vehicular cigarette lighter, said resilient arcuate contacts being positioned in spaced relationship to each other around said periphery of said cylindrical configuration, the power unit further including an outboard extent including a cylindrical sleeve slidably mounted over the outboard face of the inboard extent, the sleeve having a second pair of contacts mounted on an inner surface thereof for communicating with the first pair of contacts of the inboard extent;

a fragrance mechanism mounted on the power unit for dispensing an aroma when actuated by depressing said fragrance mechanism; and an actuation assembly including a timer mechanism for actuating the fragrance mechanism for a predetermined amount of time when actuated.

3. A heat released vehicular air freshener as set forth in claim 2 wherein the fragrance mechanism is releasably mounted to the power unit.

4. A heat released vehicular air freshener as set forth in claim 3 wherein the fragrance mechanism is releasably mounted to the power unit by way of a sleeve and post combination.

5. A heat released vehicular air freshener as set forth in claim 2 wherein the fragrance mechanism is actuated by way of heat.

* * * * *